(12) United States Patent
Kim et al.

(10) Patent No.: US 8,575,229 B2
(45) Date of Patent: Nov. 5, 2013

(54) BIOABSORBABLE BLEND FOR TEMPORARY SCAFFOLDING OF THE BLOOD VESSEL WALL

(75) Inventors: Hyung Il Kim, Seoul (KR); Kazuhiko Ishihara, Mitaka (JP)

(73) Assignees: Hyung Il Kim, Seoul (KR); Kazuhiko Ishihara, Tokyo (JP); Suntech Co., Ltd, Seoul (KR)

( * ) Notice: Subject to any disclaimer, the term of this patent is extended or adjusted under 35 U.S.C. 154(b) by 0 days.

(21) Appl. No.: 13/120,507

(22) PCT Filed: Nov. 7, 2008

(86) PCT No.: PCT/KR2008/006549
§ 371 (c)(1),
(2), (4) Date: Mar. 23, 2011

(87) PCT Pub. No.: WO2010/035920
PCT Pub. Date: Apr. 1, 2010

(65) Prior Publication Data
US 2011/0178594 A1    Jul. 21, 2011

(30) Foreign Application Priority Data
Sep. 27, 2008  (KR) .................. 10-2008-0093574

(51) Int. Cl.
*C08F 230/02* (2006.01)
*A61F 2/02* (2006.01)
*A61F 2/82* (2013.01)
*C08G 79/04* (2006.01)
*C08L 85/02* (2006.01)

(52) U.S. Cl.
USPC .......... 523/113; 424/423; 424/426; 623/1.15; 623/1.149; 623/23.7; 526/277; 525/185; 525/190; 525/538; 525/539; 525/540

(58) Field of Classification Search
USPC ......... 523/113; 424/423, 426; 623/1.15, 1.49, 623/23.7; 526/277; 525/185, 190, 538, 539, 525/540
See application file for complete search history.

(56) References Cited

U.S. PATENT DOCUMENTS 5,712,326 A   1/1998   Jones et al.
6,471,980 B2  10/2002  Sirhan et al.
(Continued)

FOREIGN PATENT DOCUMENTS

JP    2005330458    12/2005
WO    94/14897      7/1994

OTHER PUBLICATIONS

Ishihara et al., "Modification of polysulfone with phospholipid polymer for improvement of the blood compatibility. Part 1. Surface characterization", Biomaterials Sep. 1999, vol. 20, No. 17, pp. 1545-1551.

(Continued)

*Primary Examiner* — Michael Pepitone
(74) *Attorney, Agent, or Firm* — MH2 Technology Law Group, LLP

(57) ABSTRACT

A bioabsorbable blend comprising poly(L-lactide) (PLLA) and a phosphorylcholine group-containing copolymer (PPCP) capable of enduring the mechanical strength of blood vessel walls and applicable for fabricating cardiovascular devices was developed. The blend acts as a scaffold to support blood vessel walls during vascular healing and undergoes biodegradation in vivo after vascular healing is complete. Furthermore, the blend can prevent the formation and adsorption of thrombi.

19 Claims, 5 Drawing Sheets

(56) References Cited

U.S. PATENT DOCUMENTS

| | | |
|---|---|---|
| 6,663,607 B2 | 12/2003 | Slaikeu et al. |
| 7,091,213 B2 | 8/2006 | Metcalf, III et al. |
| 2005/0208093 A1* | 9/2005 | Glauser et al. ............... 424/423 |
| 2006/0106455 A1 | 5/2006 | Furst et al. |

OTHER PUBLICATIONS

Iwasaki et al., "Reduction of surface-induced inflammatory reaction on PLGA/MPC polymer blend", Biomaterials Sep. 2002, vol. 23, No. 18, pp. 3897-3903.

Khang et al. "Biocompatibility of Poly(MPC-coEHMA)/Poly(L-lactide-co-glycolide) Blends", Korea Polymer Journal, vol. 9, No. 2, pp. 107-115, Apr. 2001.

Supplementary European Search Report dated Feb. 1, 2013 issued by the European Patent Office for European Patent Application No. 08877089.6, 6 Pages.

Dauerman, Harold L. The Magic of Disappearing Stents. Journal of American College of Cardiology, vol. 58, No. 15, 2011, pp. 1589-1591.

Serruys, Patrick W. et al. Bioresorbable drug-eluting scaffolds are the future! The science behind the dream. Presented at the Transcatheter Cardiovascular Therapeutics (TCT) conference (Miami, FL) on Oct. 26, 2012, 29 Pages.

Office Action dated Apr. 3, 2013 from Japanese Patent Application No. 2011-528914 with English translation, 8 Pages.

Ueda, Tomoko et al. Preparation of 2-Methacryloyloxyethyl Phosphorylcholine Copolymers with Alkyl Methacrylates and Their Blood Compatibility. Polymer Journal, 1992, vol. 24, No. 11, pp. 1259-1269.

* cited by examiner (A) PLLA/PMB30W (95/5) cast film

← air contact surface

← mold contact surface (B) PLLA/PMB30W (90/10) cast film

← air contact surface

← mold contact surface (C) PLLA/PMB30W tube

← outer surface

← inner surface (A) outer view (B) cross-sectional view

BIOABSORBABLE BLEND FOR TEMPORARY SCAFFOLDING OF THE BLOOD VESSEL WALL

CROSS-REFERENCE TO RELATED APPLICATIONS

This application is a National Stage Application under 35 U.S.C. §371(c) of PCT Application No. PCT/KR2008/006549, filed Nov. 7, 2008, which claims the priority of Korean Patent Application No. 10-2008-0093574 filed Sep. 24, 2008, in the Republic of Korea. The entire disclosure and contents of the above applications are hereby incorporated by reference herein.

TECHNICAL FIELD

The present invention relates to a bioabsorbable blend of poly(L-lactide) (PLLA) and a phosphorylcholine group-containing copolymer (PPCP) that is capable of enduring the mechanical strength of blood vessel walls and cardiovascular devices using the blend.

BACKGROUND ART

With lifestyle changes in diet, smoking, and stress following industrialization and economic growth, the occurrence of vascular diseases such as atherosclerosis has increased rapidly. For their treatment, noninvasive interventional procedures such as percutaneous transluminal coronary angioplasty and stenting have been applied. However, the recurrence rate of vascular diseases after percutaneous transluminal coronary angioplasty is very high. Stenting can significantly lower the recurrence rate compared with traditional angioplasty and has therefore been applied more often in the recent years.

However, stenting entails several safety concerns, the most serious of which is stent thrombosis. Stent thrombosis is blood clot formation inside a stent, leading to myocardial infarction or sudden cardiac death. As this condition generally occurs more than one year after stent implantation, temporary scaffolding of blood vessel walls is required to reduce the risk of thrombosis following stent biodegradation at the implant site.

Poly(L-lactide) (PLLA) is a bioabsorbable polymer hydrolyzing into lactic acid under aqueous conditions. High-molecular-weight PLLA is known to be an adequate material for temporary scaffolding of blood vessel walls due to its relatively slow biodegradability and strong mechanical properties with respect to blood vessel walls.

U.S. Patent Publication No. 2005/0208093 discloses a composition comprising phospholipids such as phosphorylcholine, which are useful for coating of implantation devices such as drug-eluting stents. Further, U.S. Pat. No. 5,712,326 states that the biocompatibility of various polymers is improved by blending with a polymer including a zwitterionic group.

However, these conventional techniques require the coating of a metallic platform with a bioabsorbable polymer. Moreover, the conventional coating of the platform with PPCP was not efficient, which phosphorylcholine groups are not detected on the surface of conventional PPCP coated stents by an X-ray photoelectron spectroscope (XPS).

The inventors of this invention conducted various studies to solve such problems of the conventional techniques and were able to complete an invention that permits biodegradation of the stent while improving mechanical strength.

DISCLOSURE

Technical Problem

An aspect of the present invention is to provide a bioabsorbable blend capable of enduring the mechanical strength of the blood vessel wall and composed of poly(L-lactide) (PLLA) and a phosphorylcholine group-containing copolymer (PPCP), and a cardiovascular device using the blend, such as stents.

Technical Solution

In accordance with one aspect, the present invention provides a bioabsorbable blend capable of enduring the mechanical strength of the blood vessel wall and composed of PLLA and PPCP.

PLLA is a completely biodegradable polymer hydrolyzing into lactic acid in aqueous environments. It can be used as a temporary scaffold for vessel walls because its high molecular weight ensures its strong mechanical properties and relatively slow biodegradability. However, in in-vivo testing of experimental groups implanted with stents covered with a PLLA-containing coating agent, some groups suffered from a severe chronic inflammatory reaction. In some clinical studies, severe chronic inflammation occurred due to PLLA implants to secure facial bones, and most of the patients with these implants underwent reoperation for the removal of fibrous capsules containing remnant PLLA particles in the bones.

In an embodiment of the present invention, a biocompatible surface can be formed by blending PLLA with a 2-methacryloxyethyl phosphorylcholine copolymer (MPC). As phosphorylcholine groups constitute a major component of outer cell membranes, such a biocompatible surface can exhibit considerable blood compatibility in various vascular devices. One of the reasons for this behavior is that MPC copolymer is different from general hydrophilic polymers. Hydrophilic polymers interact with water on the surface, via van-der-Waals' forces, whereas MPC shows no substantial interaction with surface water. As a result, a greater amount of water is present on the surface of MPC than general hydrophilic polymers. This high fraction of free water prevents protein denaturation and adsorption as well as suppresses platelet adhesion, blood coagulation, inflammation, and so on.

Some reports have stated that when whole blood is brought in contact with aMPC, phospholipids in the plasma are immediately adsorbed onto the surface and form a stable adsorbed surface layer similar to a biomembrane, suppressing thrombus formation.

A blend of poly(L-lactide-co-glycolide) (PLGA)/MPC copolymer reduces inflammatory reactions caused by cells adsorbed onto the PLGA surface.

In this invention, a blend of bioabsorbable PLLA and a phosphorylcholine group-containing copolymer (PPCP) is prepared to improve the mechanical strength for scaffolding the blood vessel wall.

Advantageous Effects

The developed PLLA/PPCP blend provides strong breaking strength without significant change in the Young's modulus compared with the use of only PLLA under dry conditions. As a result of its high density of phosphorylcholine groups, the blend can be applied to various medical devices including stents. Furthermore, it exhibits stable biodegradation patterns through the interaction with blood components compared with PLLA alone.

BEST MODE

Figure 1:
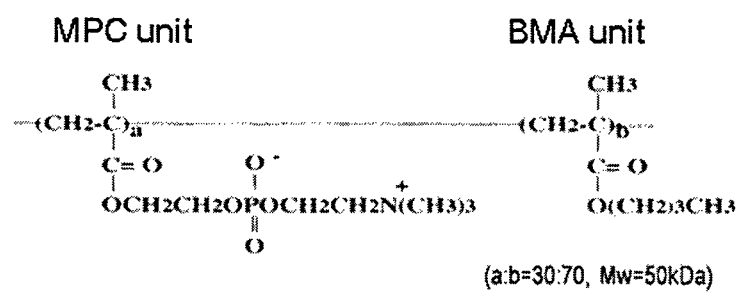
FIG. 1. Chemical structure of PMB30W.

According to this invention, a bioabsorbable blend of PLLA and PPCP was developed to improve the mechanical strength for scaffolding blood vessel walls.

PPCP can be prepared by copolymerization of MPC units with monomers selected from, but not limited to, the group consisting of methyl methacrylate (MMA), ethyl methacrylate (EMA), butyl methacrylate (BMA), 2-ethyl-hexyl methacrylate, lauryl methacrylate (LMA), hydroxyl-ethyl methacrylate (HEMA), choline methacrylate (CMA), poly (ethylene glycol) acrylate (PEGA), PEG methacrylate, 2-(methacryloxy)ethyl phosphorylcholine (MFC), N-vinyl pyrrolidone (VP), methacrylic acid (MA), acrylic acid (AA), hydroxypropyl methacrylate (HPMA), hydroxypropyl methacrylamide, 3-trimethylsilyl-propyl methacrylate (TM-SPMA), p-nitrophenyloxycarbonyl(polyoxyethylene)methacrylate (MEONP), N-isopropylacrylamide (NIPAM), and n-octyl acrylamide. More preferably, examples of the phosphorylcholine group-containing copolymer include poly(2-methacryloyloxyethyl phosphorylcholine-co-n-butyl methacrylate) (PMB30W), poly(MPC-co-BMA-co-methacrylic acid; 40,40,20) (PMBAc), poly(MPC-co-BMA; 80,20) (PMB80), poly(MPC-co-BMA-co-p-nitrophenyloxycarbonyl(polyoxyethylene)methacrylate (MEONP); 30,60,10) (PMBN) or poly(MPC-co-n-octylacrylamide-co-NIPAM; 40,30,30) (PMON). These polymers can be self-assembled into nanoparticles at a critical micelle concentration (CMC) or more in aqueous environments.

(Solvents)

It is necessary to select the optimal composition of the mixed solvents to prepare smooth membranes of PLLA and PMB30W via a solvent evaporation technique. PMB30W dissolves in methanol or ethanol but scarcely so in dichloromethane. During solvent evaporation, dichloromethane (boiling point=40.2° C.) evaporates faster than methanol (boiling point=64.7° C.) or ethanol (boiling point=78.4° C.). Because ethanol has a higher boiling point, numerous pores are formed on the mold contact surface.

(Blending Method)

Blending of PLLA and PPCP can be achieved by mechanical blending, solvent casting, latex blending, and so on.

Mechanical blending is a method of blending amorphous polymer materials above $T_g$ or blending crystalline polymer materials at $T_m$ or more. Solvent casting is a method of dissolving polymer materials in solvents followed by the removal of the solvents from the product. Latex blending is a method of blending polymer materials finely distributed in a liquid rubber (latex) to aggregate the blended polymer materials in latex.

Solvent casting enables homogeneous distribution of PPCP in PLLA, improves the mechanical strength of PLLA by bridging the aggregated crystalline regions, and provides a phosphorylcholine group-rich surface through the effects of the different boiling points on the solvents.

(Mechanical Strength)

PLLA/PMB30W (95/5, wt/wt) cast films (solvents=12/1 [v/v] dichloromethane and methanol) exhibit higher breaking strengths than PLLA cast films (solvent=dichloromethane). This feature can be explained as follows.

First, cracks are formed on the air-contact surface of PLLA cast films during solvent evaporation at room temperature, deteriorating the mechanical properties of PLLA cast films. However, as PLLA/PMB30W (95/5) cast films had a smooth surface without cracks during solvent evaporation at room temperature and pores on the surface were limited to a submicron size, PLLA/PMB30W (95/5) allows compact formation of the cylindrical polymer wall and enables it to sustain the applied deformation pressure.

Second, interlocking networks are formed between hydrophobic segments (BMA units) of PMB30W and PLLA chains. Some reports have stated that the mechanical properties of PLLA increase when blending a solution with surfactants having optimal concentrations. Therefore, in the PLLA/PMB30W (95/5) blending system, homogeneous dispersion of PMB30W can bridge the gaps between the crystalline regions of PLLA across the amorphous regions of PLLA.

(Blood Compatibility Between the Phosphorylcholine Group-Rich Surface and the Vessel Scaffold)

It is important to prepare a phosphorylcholine group-rich surface for determining the blood compatibility of the vessel scaffold. Adhesion and activation of blood cells are suppressed when the surface is coated with a high density of phosphorylcholine groups. As the mechanical properties of the PLLA/PMB30W blend should be similar to those of PLLA for scaffolding blood vessel walls, the phosphorylcholine groups cannot be coated at a high density on the surface by a conventional solvent-casting method when a small amount of PMB30W, that is, about 5 wt % or less PMB30W is blended with PLLA. Here, it should be understood that, although hydrophilic phosphorylcholine groups in the PLLA/PMB30W blend are rearranged to contact water in an aqueous environment, preparation of the phosphorylcholine group-rich surface without prior water immersion is important for the actual implantation procedure. If water immersion is performed to coat a high density of phosphorylcholine group on the surface before the implantation procedure, undesirable contamination can occur on the polymer to be implanted. By repeated coating with the dichloromethane-methanol (12/1, v/v) mixed solvent, however, a high density of PMB30W is accumulated by methanol-rich mixed solvents on the inner surface of PLLA/PMB30W tubes. Namely, a high-density phosphorylcholine group coat can be formed on the inner surface of PLLA/PMB30W tubes without water immersion. Platelet adhesion testing was conducted to determine whether a high density of phosphorylcholine groups is present on the surface of PLLA/PMB30W tubes. The results confirmed that the number of phosphorylcholine groups was reduced while platelet adhesion onto the surface was prevented.

A partially bioabsorbable and amorphous vessel support can cause serious loss of the vessel scaffold region. Water absorption from the hydrophilic phosphorylcholine groups in the PLLA/PMB30W blend can cause breakage of the ester linkages of PLLA in a pure aqueous environment. However, PLLA degradation proceeds heterogeneously and rapidly in the center where numerous carboxylic end-groups cannot diffuse, causing autocatalytic effects. Moreover, the high density of phosphorylcholine groups prevents the adsorption of blood components, but these components are absorbed in a multiple structure on PLLA. Accordingly, the phosphorylcholine groups increase discharge of carboxylic end-groups from the inner surface of PLLA/PMB30W tubes by reducing the absorption of the blood component on the surface, and may reduce the overall autocatalysis of PLLA, thereby establishing more stable biodegradation than with PLLA alone.

(Degradation Pattern)

The degradation patterns of the temporary vessel-wall scaffold vary depending on the molecular weight of PLLA, morphology of the implants, implantation sites, and scaffolding purposes. For example, PLLA stents require 2-3 years for biodegradation. Herein, as only short-term degradation patterns in in-vitro testing were studied, the results cannot be generalized to an ideal degradation pattern for the temporary vessel-wall scaffold. Because PLLA is degraded via its interaction with body components rather than simple hydrolysis, the long-term degradation behavior of the PLLA/PMB30W blend should be studied in vivo.

Therefore, the biological responses and degradation patterns of PLLA/PMB30W tubes (inner diameter=1.6 mm; outer diameter=2.0 mm) implanted in rat abdominal aorta were examined. A recent randomized clinical testing for 436 patients (ENDEAVOR III testing) in North America has revealed that phosphorylcholine group-based polymer-coated zotarolimus-eluting stents (Endeavor; Medtronics, USA) are angiographically inferior to first-generation sirolimus-eluting stents (Cypher; Cordis Johnson & Johnson, USA). This finding is due to the lack of phosphorylcholine groups on the surfaces of the Endeavor stents; no XPS was observed for phosphorous.

(Use)

From the above description, it can be understood that the novel blends with the phosphorylcholine group-rich surfaces according to this invention are very suitable for various medical devices for use in treatment of vascular diseases. Specifically, the blends with the phosphorylcholine group-rich surfaces according to this invention can be applied to vascular diseases such as angina pectoris, myocardial infarction or cardiac failure. Further, the cardiovascular devices include stents, vascular connection devices, artificial vessels, ventricular assist devices, hemopurification membranes, catheters, and the like. More specifically, the stents may be fabricated using polymer tubing or cast films of PLLA and PPCP via laser cutting or the like.

MODE FOR INVENTION

Next, the invention will be described in detail with reference to examples.

It should be noted that the following examples are given by way of illustration of the invention and the present invention is not limited to these examples.

EXAMPLE 1

Preparation of PLLA/PMB30W Blends

High-molecular-weight PLLA (Mw=100 kDa) and low-molecular-weight PLLA (sPLLA; Mw=2 kDa) were obtained from Polysciences. Water-soluble amphiphilic PMB30W (Mw=50 kDa) was synthesized from an MPC unit and a BMA unit at a ratio of 3 to 7. The chemical structure of PMB30W is shown in FIG. 1. A 6 wt % PLLA polymer solution in dichloromethane, PLLA/PMB30W (95/5, wt/wt) blend polymer solution in dichloromethane and methanol (12/1, v/v), and PLLA/PMB30W (90/10, wt/wt) blend polymer solution in dichloromethane and methanol (12/1, v/v) were prepared, followed by sufficient stirring of the solutions until they became transparent. The solutions were sonicated in a cold bath with ice for 30 min for homogenization.

EXAMPLE 2

Fabrication of PLLA/PMB30W Cast Films and Tubes

To fabricate cast films, the polymer solutions were cast onto Teflon dishes, and the solvents were dried overnight at room temperature.

The PLLA polymer solution was dip-coated on Teflon rods of 1.6-4.0 mm diameter to fabricate small and large tubes, respectively. The large tubes were processed only for XPS surface analysis and blood contact testing. The solvent was evaporated from the Teflon rods by rotating at 70-80 rpm for 1 h at room temperature. This process was repeated 7-8 times to fabricate a small tube having an outer diameter of 2.0 mm.

The PLLA/PMB30W (95/5, wt/wt) blend polymer solution was dip-coated on Teflon rods of 1.6-4.0 mm in diameter. The solvent was evaporated from the Teflon rods by rotating at 70-80 rpm for 1 h at room temperature. This process was repeated 9 times to fabricate a thick polymer membrane acting as a mechanical supporting layer of the PLLA/PMB30W tube. Subsequently, the PLLA/PMB30W (95/5, wt/wt) tube was dip-coated once with the PLLA/PMB30W (90/10, wt/wt) blend polymer solution to form a surface having a high density of phosphorylcholine groups. The solvent was evaporated overnight from the Teflon rods by rotating at 70-80 rpm at room temperature. The outer diameter of small PLLA/PMB30W tubes was 2.0 mm. All samples were dried in vacuo at room temperature for a day, followed by drying in vacuo at 60° C. for 2 days. The samples were then stored in vacuo before use.

EXAMPLE 3

Methods for Determining the Properties of PLLA/PMB30W Blends (Morphology)

The samples were subjected to gold sputtering, followed by observation of the surface morphologies under a scanning electron microscope (SEM; SM-200; Topcon, Japan).

(Mechanical Properties)

The cast films were cut into barbell-shaped films (44.5 mm×2.5 mm). The breaking strength and Young's modulus of the barbell-shaped cast films were measured with a strength tester (STA-1150; Orientec, Japan). The crosshead speed was 10 mm/min.

(Surface Analysis)

A large PLLA/PMB30W tube was cut into concave membranes before the removal of residual solvents. To fabricate flat membranes, the concave membranes were pressed by applying a pressure of 10 MPa at 60° C. for 10 min. After removing the residual solvents, the flat membranes were incubated with phosphate-buffered saline (PBS) at 36.7° C. in a shaking bath at 80-100 rpm. The flat membranes were then sufficiently rinsed with distilled water after incubation for several times. The surfaces of these membranes were analyzed by using an X-ray photoelectron spectroscope (XPS; AXIS-Hsi; Kratos/Shimadzu, Japan) with an Mg Kα source (1253.6 eV). The take-off angle of the photoelectron was 90°.

Figure 2:
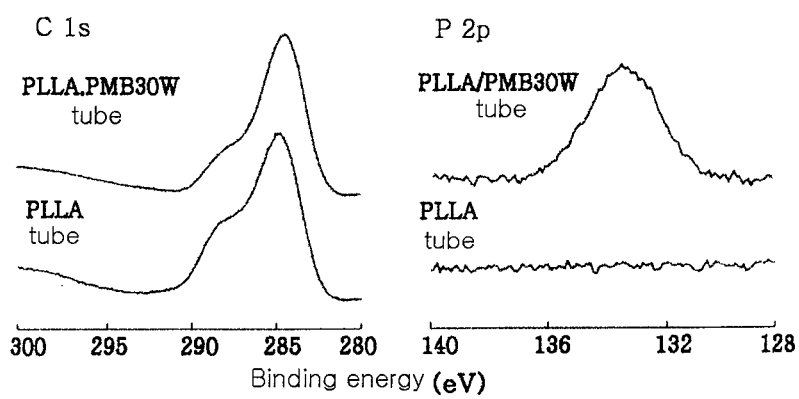
FIG. 2. The $C_{1s}$ and $P_{2p}$ peaks obtained from the inner surface of a PLLA/PMB30W tube and a PLLA tube by using an X-ray photoelectron spectroscope (XPS) with Mg Kα radiation (1253.6 eV).

FIG. 2 shows the $C_{1s}$ and $P_{2p}$ peaks from the inner surfaces of the PLLA and PLLA/PMB30W tubes. The strong $P_{2p}$ peaks at 134 eV were attributed to phosphorus in the phosphorylcholine groups. The P/C percentage ratios of the PLLA/PMB30W tubes were calculated on the basis of the amount of phosphorous and concentration of carbon atoms.

(Platelet Adhesion Test)

The tubes were cut into 0.5-cm-long pieces by using a tube cutter. Fresh human whole blood (45 mL) was collected from a healthy volunteer in a syringe containing 5 mL of acid-citrate-dextrose A solution. Platelet-rich plasma (PRP) was prepared through centrifugation at 200 g for 15 min. The platelet concentration obtained was $4.24 \times 10^5$ platelets/μL, measured with a cell counter. Each tube was immersed in 200 μL of PRP. The top layer of PRP was covered with a Teflon sheet to immerse the tubes completely. The tubes were placed in an incubator of 5% $CO_2$ atmosphere at 37° C. for 1 h. Each tube was then immersed in 15 mL of PBS for 3 min for removing the nonadhered platelets and placed in 200 μL of PBS containing 1% (v/v) Triton-X114 solution at 37° C. for 1 h to dissolve the adhered platelets. The amount of released lactate dehydrogenase (LDH) was measured by using an LDH assay kit (Wako Pure Chemicals, Japan) according to manufacturer's instructions. The control group was PBS containing 1% (v/v) Triton-X114 solution.

(Short-Term Degradation Pattern)

1. Saline Testing

The cast films were cut into $1 \times 1$ $cm^2$ pieces and the tubes were cut into 0.5-cm-long pieces by using a tube cutter. The initial dry weight of each cast film and tube was measured. The cast films and tubes were then incubated in PBS at 36.7° C. in a shaking bath at 80-100 rpm. The samples were removed from the bath, rinsed thoroughly with distilled water, and completely dried in vacuo for a day at 60° C. The dry weights of the incubated samples were measured by using a gravimetric method. The overall mass change percentage was calculated from the following equation:

Overall mass change percentage={(initial mass−reweighed mass after incubation)/initial mass}×100

2. Serum Testing

PLLA/sPLLA (4/1, wt/wt) was blended with PMB30W by the aforementioned method. Tubes were fabricated and cut into 1.5-cm-long pieces by using a tube cutter. They were incubated in 2 mL of fetal bovine serum (FBS) using the aforementioned method. A penicillin-streptomycin-amphotericin B mixture was added to the medium to prevent bacterial contamination and the medium was changed every 3 days.

After 20 days of incubation, the tubes were removed from the incubator and rinsed with distilled water. The tubes were sonicated in a 1% sodium dodecyl sulfate aqueous solution for 20 min to remove the absorbed serum components, rinsed with distilled water, and then dried in vacuo at 60° C. for a day. The overall mass change percentage was calculated by using the previously stated equation.

Results

1. Mechanical Properties of PLLA/PMB30W Cast Films

Figure 3:
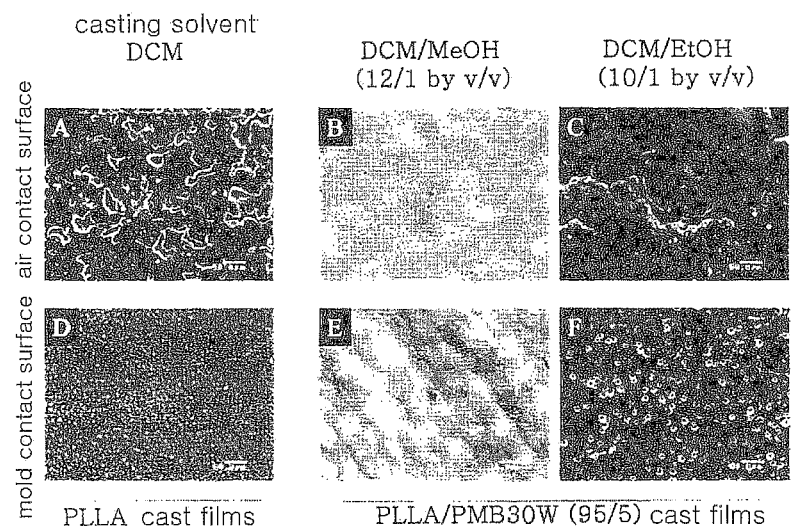
FIG. 3. Scanning electron microscope (SEM) images of PLLA/PMB30W cast films.

To obtain the optimal casting solvent for the preparation of PLLA/PMB30W blends, various PLLA/PMB30W cast films were prepared with various mixed solvents. The PLLA cast (solvent=dichloromethane) films exhibited several cracks on their air-contact surface (FIGS. 3A and 3D). The PLLA/PMB30W cast films with dichloromethane and methanol (12/1, v/v) as solvents exhibited fine smooth surfaces (FIGS. 3B and 3E), whereas the PLLA/PMB30W cast films with dichloromethane and ethanol (10/1, v/v) as solvents had relatively rough surfaces with numerous micron-sized pores (FIGS. 3C and 3F). Both the PLLA/PMB30W blends (95/5 and 90/10, wt/wt) exhibited identical surface morphology. A thrombus is likely form particularly on the surface cracks where the blood flows slowly and undergoes high resistance. To prepare a polymer wall for providing mechanical support to blood vessel walls, dichloromethane and methanol (12/1, v/v) were used as solvents to cast the PLLA/PMB30W blends.

Figure 4:
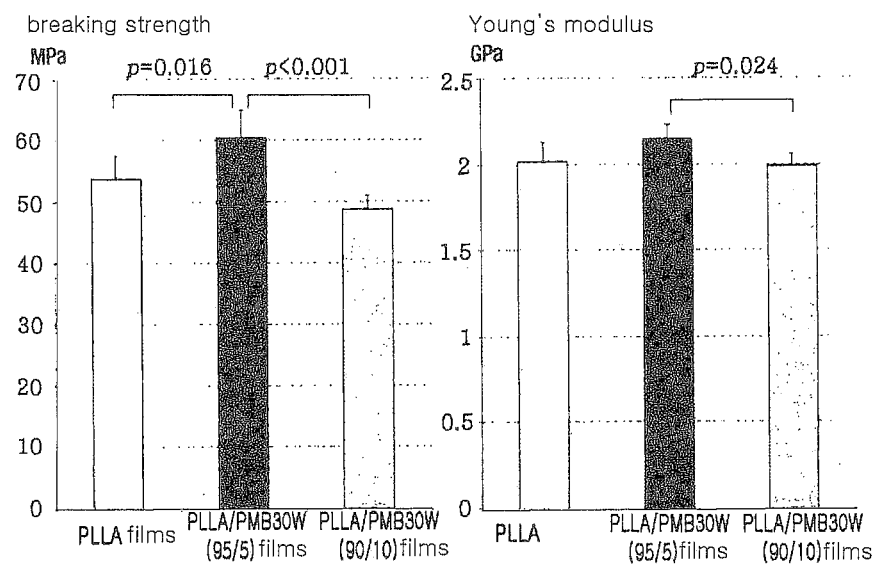
FIG. 4. The mechanical properties of PLLA/PMB30W cast films. The error bars indicate standard deviations for n=6. Statistical differences were obtained by using Tukey's test after ANOVA and considered significant at p<0.05.

FIG. 4 shows the mechanical properties of the cast films before incubation. The PLLA/PMB30W (95/5, wt/wt) cast films exhibited higher breaking strengths whereas the PLLA/PMB30W (90/10, wt/wt) cast films exhibited lower breaking strengths than the PLLA cast films. The Young's modulus of the PLLA/PMB30W (95/5, wt/wt) and PLLA/PMB30W (90/10, wt/wt) cast films was not significantly different from that of the PLLA cast films, but the Young's modulus of the PLLA/PMB30W (95/5, wt/wt) cast films was higher than that of the PLLA/PMB30W (90/10, wt/wt) cast films. The overall mass change of the PLLA/PMB30W (90/10, wt/wt) cast films was significantly greater than that of the other cast films during incubation in PBS (Table 1).

TABLE 1

|  | PLLA film | PLLA/PMB30W (95/5) film | PLLA/PMB30W (90/10) film |
|---|---|---|---|
| Count | 5.00 | 5.00 | 4.00 |
| Mean (%) | 0.28 | 0.35 | 3.84 |
| Standard deviation (%) | 0.27 | 0.20 | 0.80 |

Figure 5:
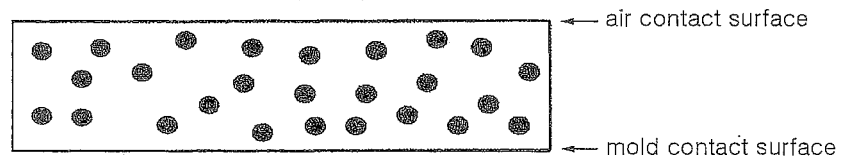
FIG. 5. Distribution of phosphorylcholine groups in PLLA/PMB30W cast films and PLLA-PMB30W tubes. The dark circles indicate the phosphorylcholine groups in PMB30W.
Figure 5:
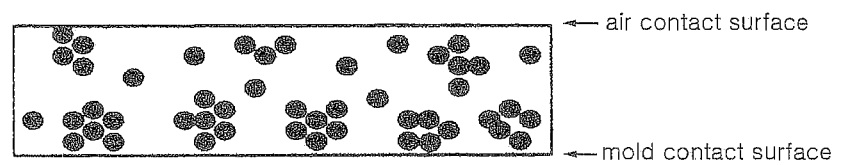
Figure 5:
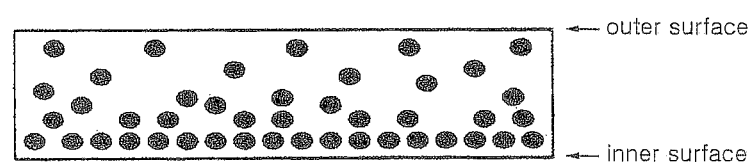

Water-soluble PMB30W was considered to have aggregated in the PLLA/PMB30W (90/10) blend system (FIG. 5B, Table 2).

TABLE 2

| Sample | Surface | Compositions (wt/wt) | P/C values (%) (mean ± SD) | |
|---|---|---|---|---|
|  |  |  | Preincubation | After 1-week incubation |
| PLLA/ PMB30W cast film | Air contact | 95/5 | 0.19 ± 0.03 | 0.32 ± 0.11 |
|  | Air contact | 90/10 | 0.27 ± 0.17 | 0.75 ± 0.15 |
|  | Mold contact | 95/5 | 0.20 ± 0.07 | 0.38 ± 0.07 |
|  | Mold contact | 90/10 | 1.12 ± 0.14 | 1.24 ± 0.32 |
| PLLA/ PMB30W tube | Outer | ND | 0.24 ± 0.22 | 0.27 ± 0.15 |
|  | Inner | ND | 0.92 ± 0.10 | 1.08 ± 0.11 |

Figure 6:
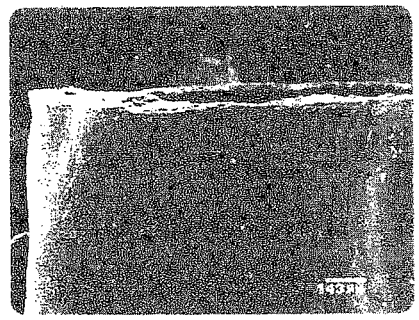
FIG. 6. Scanning electron microscope (SEM) images of PLLA/PMB30W tubes.
Figure 6:
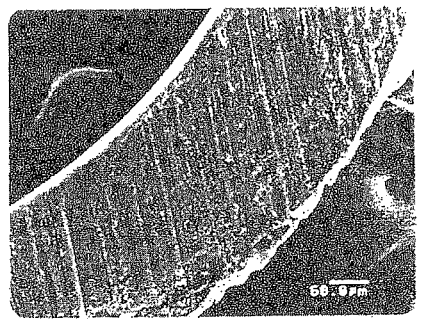

Consequently, the blend ratio of 95/5 for PLLA/PMB30W was considered the most suitable for constructing a mechanical support layer with PLLA/PMB30W tubes (FIG. 6).

2. XPS Analysis of the Inner Surface of PLLA/PMB30W Tubes

Figure 7:
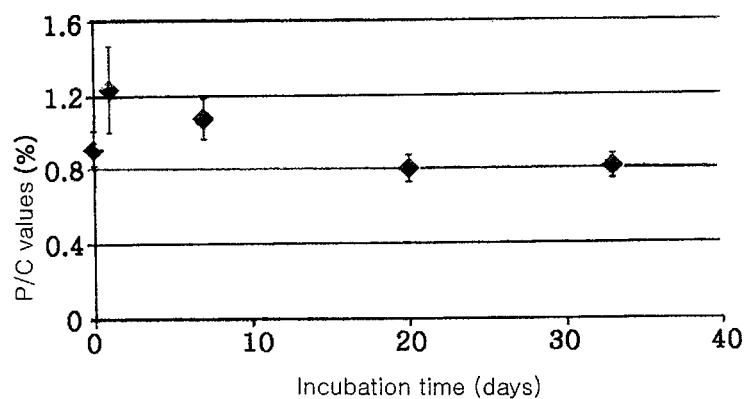
FIG. 7. Variations in the P/C values on the inner surface of PLLA/PMB30W tubes during the incubation in PBS. The data points and whiskers indicate the mean and standard deviation for 6≤n≤9, and the asterisks indicate a statistically significant difference from day 0 (Dunnett's test after ANOVA, p<0.05).

The phosphorylcholine groups on the surface of the PLLA/PMB30W tubes were analyzed by using an XPS. FIG. 2 shows the $C_{1s}$ and $P_{2p}$ peaks on the inner surfaces of the PLLA and PLLA/PMB30W tubes. The strong $P_{2p}$ peaks at 134 eV were attributed to phosphorus in the phosphorylcholine groups. The P/C values of the PLLA/PMB30W tubes were calculated on the basis of the amount of phosphorous and concentration of carbon atoms. FIG. 7 shows the change in the P/C values (%) on the inner surface of the PLLA/PMB30W tubes during incubation in PBS. The P/C values were high on the first day of incubation and then equilibrated. The increase in the concentration of methanol in the mixed solvent by solvent evaporation provided the phosphorylcholine-rich surface.

Figure 8:
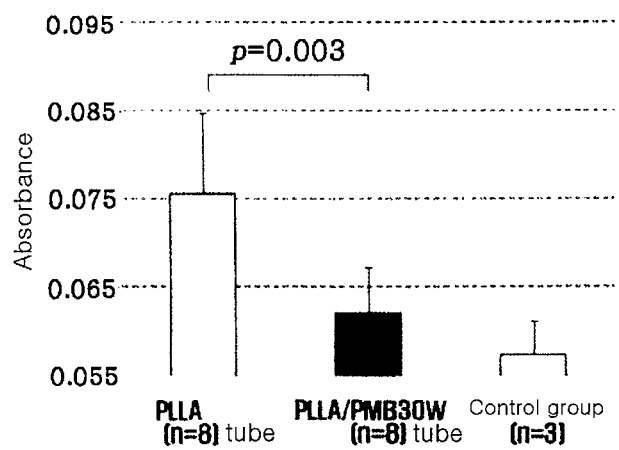
FIG. 8. The results of the platelet adhesion test. The error bars indicate standard deviations. The statistical importance was analyzed by ANOVA.

The high density of phosphorylcholine groups on the inner surface of the PLLA/PMB30W tubing could reduce platelet adhesion after contact with PRP (FIG. 8). Both the PLLA and PLLA/PMB30W tubes showed slow overall mass change over the 100 days of incubation in PBS (Table 3).

TABLE 3

|  | PLLA tube | PLLA/PMB30W tube |
|---|---|---|
| Count | 5.00 | 5.00 |
| Mean (%) | 2.20 | 1.24 |
| Standard deviation (%) | 1.32 | 1.89 |

To promote heterogeneous degradation, sPLLA was blended into the tubes. The promoted overall mass change was not significantly different between the two groups after 20 days of incubation in PBS or FBS (Tables 4 and 5).

Table 4 shows the promoted overall mass change percentage of the tubes with sPLLA after 20 days of incubation in PBS, and Table 5 shows the promoted overall mass change percentage after 20 days of incubation in FBS.

TABLE 4

|  | PLLA/sPLLA tube | PLLA/sPLLA/PMB30W tube |
|---|---|---|
| Count | 5.00 | 5.00 |
| Mean (%) | 1.15 | 1.62 |
| Standard deviation (%) | 1.08 | 1.71 |

TABLE 5

|  | PLLA/sPLLA tube | PLLA/sPLLA/PMB30W tube |
|---|---|---|
| Count | 7.00 | 5.00 |
| Mean (%) | 1.14 | 1.49 |
| Standard deviation (%) | 1.44 | 1.25 |

EXAMPLE 4

Preparation of Other PLLA/PPCP Blends

PMBN (Mw=58 kDa) and PMB80 (Mw=40 kDa) were used to prepare PLLA/PPCP blends by the same method as described in Example 1.

EXAMPLE 5

Fabrication of PLLA/PPCP Cast Films with Example 4

The respective PLLA/PPCP polymer solutions described in Example 4 in dichloromethane and methanol (12/1, v/v) were prepared by stirring the solutions overnight. The solutions were sonicated in a cold bath with ice for 30 min for homogenization. To fabricate cast films, the polymer solutions were cast onto Teflon dishes, and the solvents were dried overnight at room temperature. All samples were dried in vacuo at room temperature for a day, followed by drying in vacuo at 60° C. for two days. The samples were stored in vacuum desiccators before use.

Results

Figure 9:
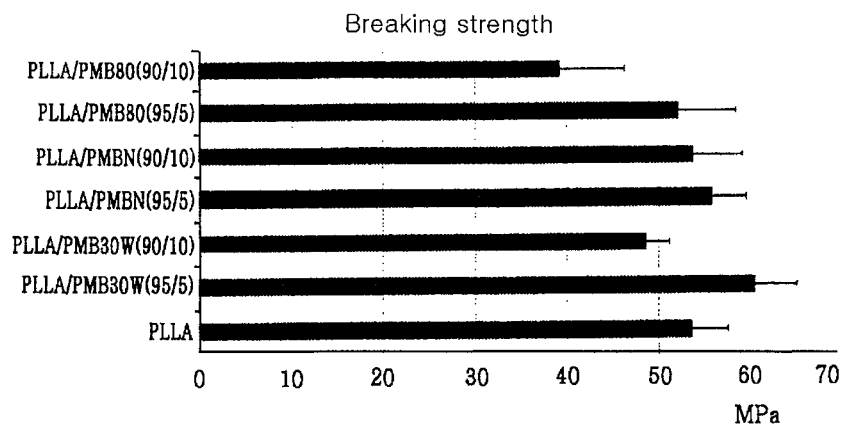
FIG. 9. The breaking strengths of the PLLA/PPCP blends.

The results of the breaking strengths of the PLLA/PPCP blend cast films fabricated in Example 4 are shown in Table 6 and FIG. 9. Not only the PLLA/PMB30W (95/5, wt/wt) cast films but also the PLLA/PMBN (95/5, wt/wt) and PLLA/PMB80 (95/5, wt/wt) cast films exhibited superior breaking strengths than the PLLA or PLLA/PPCP (90/10, wt/wt) cast films.

TABLE 6

| Polymer | PLLA | PLLA/PMB30W | | PLLA/PMBN | | PLLA/PMB80 | |
|---|---|---|---|---|---|---|---|
| Blend ratio (wt/wt) |  | 95/5 | 90/10 | 95/5 | 90/10 | 95/5 | 90/10 |
| Mean (MPa) | 53.68 | 60.58 | 48.73 | 55.89 | 53.86 | 52.25 | 39.31 |
| Standard deviation (MPa) | 3.91 | 4.60 | 2.48 | 3.64 | 5.31 | 6.24 | 6.95 |

EXAMPLE 6

Preparation of Other PLLA/PMB30W Blends with Different Blend Ratios

PLLA/PMB30W blends containing 0.5 wt %, 2 wt %, 5 wt %, 7 wt %, 8 wt %, and 10 wt % PMB30W copolymer were prepared in the same manner as described in Example 1.

EXAMPLE 7

Fabrication of PLLA/PMB30W Cast Films with Example 6

PLLA/PMB30W cast films were fabricated in the same manner as described in Example 5.

Results

Figure 10:
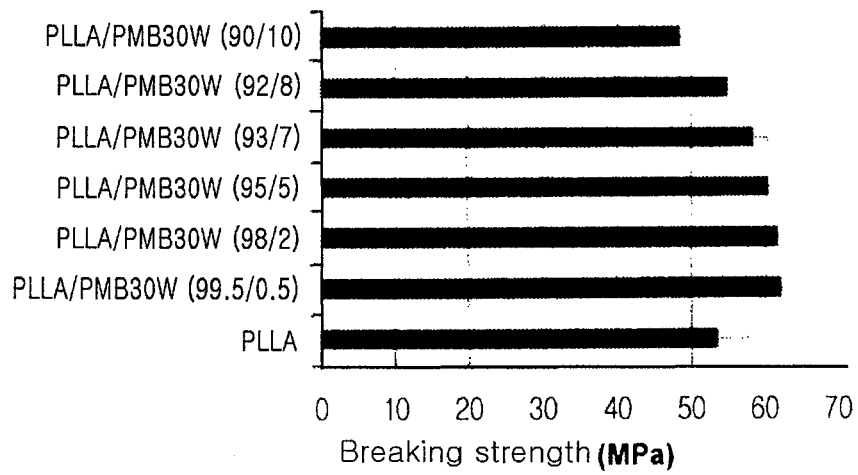
FIG. 10. The breaking strengths of PLLA/PMB30W cast films having various blend ratios.

The results of the breaking strengths of the PLLA/PPCP cast films fabricated via the method in Example 6 are shown in Table 7 and FIG. 10. It can be seen that PLLA/PMB30W blend cast films containing 0.5~8 wt % PMB30W copolymer exhibited superior breaking strengths than the PLLA or PLLA/PPCP (90/10, weight ratio) cast films.

TABLE 7

| Polymer | PLLA | PLLA/PMB30W | | | | | |
|---|---|---|---|---|---|---|---|
| Blend ratio (wt/wt) | | 99.5/0.5 | 98/2 | 95/5 | 93/7 | 92/8 | 90/10 |
| Mean (MPa) | 53.68 | 62.27 | 61.81 | 60.58 | 58.55 | 55.15 | 48.73 |
| Standard deviation (MPa) | 3.91 | 3.18 | 4.80 | 4.60 | 1.90 | 3.47 | 2.48 |

INDUSTRIAL APPLICABILITY

The blend composed of PLLA and PPCP provides higher breaking strength than the PLLA copolymer without significant change in the Young's modulus under dry conditions and has a high density of phosphorylcholine groups on the inner surface to exhibit superior biocompatibility. Therefore, this blend can be applied to various medical devices including biodegradable stents.

The invention claimed is:

1. A bioabsorbable blend, the blend comprising PLLA (poly(L-lactide)) and a phosphorylcholine group-containing copolymer (PPCP).

2. The blend according to claim 1, wherein the PPCP is a water-soluble amphiphilic copolymer.

3. The blend according to claim 1, wherein the PPCP is prepared by copolymerization of a 2-methacryloyloxethyl phosphoroylcholine (MPC) unit with a monomer selected from the group consisting of methyl methacrylate (MMA), ethyl methacrylate (EMA), butyl methacrylate (BMA), 2-ethylhexyl methacrylate (EHMA), lauryl methacrylate (LMA), hydroxyl-ethyl methacrylate (HEMA), choline methacrylate (CMA), poly(ethylene gycol) acrylate (PEGA), PEG methacrylate, 2-(methacryloxy)ethyl phosphorylcholine (MFC), N-vinyl pyrrolidone (VP), methacrylic acid (MA), acrylic acid (AA), hydroxypropyl methacrylate (HPMA), hydroxypropyl methacrylamide, 3-trimethylsilyl-propyl methacrylate (TMSPMA), p-nitrophenyloxycarbonyl(polyoxyethylene) methacrylate (MEONP), N-isopropylacrylamide (NIPAM), N-octyl acrylamide, and a combination thereof.

4. The blend according to claim 2, wherein the PPCP is selected from the group consisting of poly(2-methacryloyloxyethyl phosphorylcholine-co-n-butyl methacrylate) (PMB), poly(MPC-co-BMA-co-methacrylic acid) (PMBAc), poly(MPC-co-BMA), poly(MPC-co-BMA-co-p-nitrophenyloxycarboxyl (polyoxyethylene) methacrylate (MEONP)) (PMBN), poly(MPC-co-n-octylacrylamide-co-NIPAM) (PMON) poly(MPC-co-BMA-co-MEONP) (PMBN), and poly(MPC-co-n-octylacrylamide-co-NIPAM) (PMON).

5. The blend according to claim 1, wherein the blend comprises 0.5 wt % to 8 wt % PPCP with respect to the total weight of the blend.

6. The blend according to claim 1, wherein the PLLA and PPCP are blended using a solvent casting technique.

7. The blend according to claim 6, wherein the solvent comprises dichloromethane and methanol.

8. A cardiovascular device for treating a cardiovascular disease comprising the bioabsorbable blend according to claim 1.

9. The cardiovascular device according to claim 8, wherein the cardiovascular device is an artificial vessel, a stent, a vascular anastomotic device, a ventricular assist device, a hemopurification membrane, or a catheter.

10. The cardiovascular device according to claim 8, wherein the cardiovascular device is a biodegradable stent.

11. The cardiovascular device according to claim 8, wherein the cardiovascular disease is selected from the group consisting of atherosclerosis, thrombosis, restenosis, hemorrhage, vascular dissection or perforation, vascular aneurysm, vulnerable plaque, chronic total occlusion, claudication, anastomotic proliferation for vein and artificial grafts, bile duct obstruction, ureter obstruction, tumor obstruction, and a combination thereof.

12. The cardiovascular device according to claim 9, wherein the cardiovascular device is a stent fabricated by processing a tube made of the bioabsorbable blend.

13. The cardiovascular device according to claim 9, wherein the cardiovascular device is a stent fabricated by processing a cast film made of the bioabsorbable blend.

14. The cardiovascular device according to claim 10, wherein the cardiovascular device is a stent fabricated by processing a tube made of the bioabsorbable blend.

15. The cardiovascular device according to claim 10, wherein the cardiovascular device is a stent fabricated by processing a cast film made of the bioabsorbable blend.

16. The cardiovascular device according to claim 11, wherein the cardiovascular device is a stent fabricated by processing a tube made of the bioabsorbable blend.

17. The cardiovascular device according to claim 11, wherein the cardiovascular device is a stent fabricated by processing a cast film made of the bioabsorbable blend.

18. A bioabsorbable stent comprising the blend according to claim 1.

19. The bioabsorbable stent according to claim 18, wherein the phosphorylcholine group containing copolymer (PPCP) is absorbable in blood.

* * * * *

UNITED STATES PATENT AND TRADEMARK OFFICE
CERTIFICATE OF CORRECTION

PATENT NO. : 8,575,229 B2
APPLICATION NO. : 13/120507
DATED : November 5, 2013
INVENTOR(S) : Hyung-Il Kim and Kazuhiko Ishihara It is certified that error appears in the above-identified patent and that said Letters Patent is hereby corrected as shown below:

Title page, item (30), entitled Foreign Application Priority Data, the filing date "Sept. 27, 2008" should read --Sept. 24, 2008--.

Signed and Sealed this
Eighteenth Day of February, 2014

Michelle K. Lee
*Deputy Director of the United States Patent and Trademark Office*